US012539225B2

(12) United States Patent
Ostergard

(10) Patent No.: US 12,539,225 B2
(45) Date of Patent: *Feb. 3, 2026

(54) HINGED ANKLE BRACE

(71) Applicant: Doak Ostergard, Lincoln, NE (US)

(72) Inventor: Doak Ostergard, Lincoln, NE (US)

( * ) Notice: Subject to any disclaimer, the term of this patent is extended or adjusted under 35 U.S.C. 154(b) by 211 days.

This patent is subject to a terminal disclaimer.

(21) Appl. No.: 18/410,039

(22) Filed: Jan. 11, 2024

(65) Prior Publication Data

US 2024/0139014 A1 May 2, 2024

Related U.S. Application Data

(63) Continuation of application No. 17/130,338, filed on Dec. 22, 2020, now Pat. No. 11,877,944, which is a continuation-in-part of application No. 15/367,929, filed on Dec. 2, 2016, now Pat. No. 11,045,343.

(51) Int. Cl.
*A61F 5/01* (2006.01)

(52) U.S. Cl.
CPC .... *A61F 5/0127* (2013.01); *A61F 2005/0137* (2013.01); *A61F 2005/0165* (2013.01)

(58) Field of Classification Search
CPC ...... A61F 2005/0148; A61F 2005/0179; A61F 2005/0165; A61F 2005/0169; A61F 2005/0197; A61F 5/0111; A61F 5/0113; A61F 5/0106; Y10T 403/455; Y10T 403/454; Y10T 403/32541; Y10T 403/32549; Y10T 403/32557; Y10T 403/45; Y10T 403/458; A63B 21/4025; A63B 21/4013; A63B 21/04-0407; A63B 21/0421; A63B 21/045
USPC ............................................. 403/22; 602/16
See application file for complete search history.

(56) References Cited

U.S. PATENT DOCUMENTS

| | | | | |
|---|---|---|---|---|
| 4,934,355 | A | 6/1990 | Porcelli | |
| 5,069,202 | A | 12/1991 | Prock | |
| 5,209,716 | A | 5/1993 | Frydman et al. | |
| 5,263,911 | A * | 11/1993 | Frydman | A63B 23/08 482/79 |
| 7,753,866 | B2 | 7/2010 | Jackovitch | |
| 8,641,654 | B2 | 2/2014 | Verkade et al. | |
| 9,364,366 | B2 | 6/2016 | Verkade et al. | |
| 10,226,373 | B1 | 3/2019 | McCoy | |
| 2006/0009722 | A1 | 1/2006 | Seligman | |
| 2006/0084899 | A1 | 4/2006 | Verkade et al. | |
| 2011/0226385 | A1 | 9/2011 | Mitchell et al. | |
| 2013/0075966 | A1 | 3/2013 | Carvey et al. | |
| 2014/0066829 | A1 | 3/2014 | Drillio | |
| 2015/0216703 | A1 | 8/2015 | Madden et al. | |
| 2018/0153724 | A1 * | 6/2018 | Ostergard | A61F 5/0127 |

FOREIGN PATENT DOCUMENTS

WO 2010070364 A1 6/2010

* cited by examiner

*Primary Examiner* — Tarla R Patel
(74) *Attorney, Agent, or Firm* — Stinson LLP

(57) ABSTRACT

A hinged ankle brace including a foot bed member and an ankle cuff which are hinged together by flexible joint members. The flexible joint members yieldably resist hinged movement between the foot bed member and the ankle cuff in a plantarflexion and dorsiflexion direction. The design of the upper ends of the medial and lateral wings of the foot bed member and the ankle cuff permit a limited amount of inversion and eversion movement between the foot bed member and the ankle cuff.

14 Claims, 13 Drawing Sheets

HINGED ANKLE BRACE

CROSS REFERENCE TO RELATED APPLICATION

This is a Continuation-In-Part Application of application Ser. No. 15/367,929 filed Dec. 2, 2016, entitled A HINGED ANKLE BRACE.

BACKGROUND OF THE INVENTION

Field of the Invention

This invention relates to a hinged ankle brace and more particularly to a hinged ankle brace wherein the medial and lateral joints between the foot bed member and the ankle cuff are flexible joint members comprised of polyurethane or like materials. Even more particularly, the flexible joint members create greater resistance to hinged movement of the foot bed member and the ankle cuff thereof as the two members hingedly move to a greater degree with respect to one another. Even more particularly, the flexible joint members and related structure not only permit plantarflexion and dorsiflexion hinged movement between the foot bed member and the ankle cuff but also permit inversion and eversion movement therebetween.

DESCRIPTION OF THE RELATED ART

Conventional semi-rigid ankle braces have been previously provided wherein the foot bed member of the ankle brace is pivotally or hingedly movable, about a pair of joints, with respect to the ankle cuff of the brace or vice versa. Normally, each of the prior art joints between the foot bed member and the ankle cuff are simply a pivot pin or bolt. In such braces, the pivotal movement between the foot bed member and the ankle cuff is not a floating movement but is a pivotal movement about a central axis. Further, to the best of Applicant's knowledge, no one has provided a joint for hinged ankle braces which increases the resistance to pivotal movement as the pivotal movement between the foot bed member and the ankle cuff increases. In other words, in the prior art, any resistance to the pivotal movement between the foot bed member and the ankle cuff, if any, remains the same during the entire pivotal movement therebetween.

Applicant's hinged ankle brace of Published Application U.S. 2018/0153724 A1 represents a significant advance in the ankle brace art in that the flexible joint members thereof create greater resistance to hinged movement of the foot bed member and the ankle cuff thereof as the two members hingedly move to a greater degree with respect to one another. However, the flexible joint members of the co-pending application only permit plantarflexion and dorsiflexion movement of the foot bed member and the ankle cuff thereof. Applicant has determined that it is advantageous to also permit some inversion and eversion movement between the foot bed member and the ankle cuff thereof.

SUMMARY OF THE INVENTION

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

The hinged ankle brace of this invention includes a foot bed member having a foot plate configured to underlie at least a portion of the foot of the wearer and a portion configured to receive a heel of the wearer. For purposes of description, the foot bed member will be described as having a medial side and a lateral side. The hinged ankle brace of this invention will be described as being attached to the left ankle and foot of the wearer. If the hinged ankle brace of the invention is attached to the right ankle and foot of the wearer, the medial side of the foot bed member will become the lateral side of the foot bed member and the lateral side of the foot bed member will become the medial side of the foot bed member.

A medial wing extends upwardly from the medial side of the foot bed member with the medial wing having a semi-circular upper end with inner and outer sides. The inner side of the upper end of the medial wing of the foot bed member is outwardly curved. The outer side of the upper end of the medial wing of the foot bed member is outwardly curved or domed. The upper end of the medial wing of the foot bed member has radially spaced-apart first, second and third curved slots formed therein. The upper end of the medial wing of the foot bed member has a central section with a central opening formed therein. Radially spaced-apart first, second and third pin members extend outwardly from the outer side of the central section thereof.

A lateral wing extends upwardly from the lateral side of the foot bed member and has a generally semi-circular upper end with inner and outer sides. The inner side of the upper end of the lateral wing of the foot bed member is outwardly curved. The outer side of the lateral wing is outwardly curved or domed. The upper end of the lateral wing of the foot bed member has radially spaced-apart first, second and third curved slots formed therein. The lateral wing of the foot bed member has a central section with a central opening formed therein. Radially spaced-apart first, second and third pin members extend outwardly from the outer side of the central section thereof.

The ankle brace also includes an ankle cuff, having upper and lower ends, including a leg-supported portion configured to extend at least partially around the posterior side of the lower leg of a wearer. The ankle cuff has a medial side and a lateral side. The ankle cuff has a medial wing which extends downwardly from the medial side thereof. The medial wing of the ankle cuff has a generally semi-circular lower end with inner and outer sides. The inner side of the medial wing of the ankle cuff is outwardly curved. The outer side of the medial wing of the ankle cuff is outwardly curved or domed. The lower end of the medial wing of the ankle cuff has radially spaced-apart first, second and third curved slots formed therein. The lower end of the medial wing of the ankle cuff has a central section with a central opening formed therein. Radially spaced-apart first, second and third pin members extend inwardly from the inner side of the lower end of the medial wing of the ankle cuff.

The ankle cuff also has a lateral wing extending downwardly from the lateral side thereof. The lateral wing of the ankle cuff has a generally semi-circular lower end with inner and outer sides. The inner side of the lateral wing of the ankle cuff is outwardly curved. The outer side of the lateral wing of the ankle cuff is outwardly curved or domed. The lower end of the lateral wing of the ankle cuff has radially spaced-apart first, second and third curved slots formed therein. The lower end of the lateral wing of the ankle cuff has a central section with a central opening formed therein. Radially spaced-apart first, second and third pin members extend inwardly from the inner side of the lower end of the lateral wing of the ankle cuff.

The inner side of the lower end of the medial wing of the ankle cuff is positioned outwardly of the outer side of the upper end of the medial wing of the foot bed member. The inner side of the lower end of the lateral wing of the ankle cuff is positioned outwardly of the outer side of the upper end of the lateral wing of the foot bed member.

A flat flexible medial joint member is positioned between the lower end of the medial wing of the ankle cuff and the upper end of the medial wing of the foot bed member. The flexible medial joint member includes a central base portion having radially spaced-apart first, second and third pin openings formed therein. The base portion of the flexible medial joint member has a central opening formed therein. The flexible medial joint member has radially spaced-apart first, second and third arms with inner and outer ends, extending outwardly from the base portion thereof. Fourth, fifth and sixth pin openings are formed in the outer ends of the first, second and third arms respectively.

As stated, the flexible medial joint member is positioned at the inner side of the lower end of the medial wing of the ankle cuff. When so positioned, the first, second and third pin members, which extend inwardly from the inner side of the lower end of the medial wing of the ankle cuff, are received in the fourth, fifth and sixth pin openings in the flexible medial joint member respectively. In that position, the first, second and third pin openings in the flexible medial joint member register with the first, second and third slots formed in the lower end of the medial wing of the ankle cuff and the central opening in the base portion of the flexible medial joint member registers with the central opening formed in the central section of the lower end of the medial wing of the ankle cuff. A connector element, such as a rivet or the like, extends through the central opening in the lower end of the medial wing of the ankle cuff, through the central opening in the base portion of the flexible medial joint member and through the central opening in the central section of the upper end of the medial wing of the foot bed member to hingedly connect the medial wing of the foot bed member to the medial wing of the ankle cuff.

A flexible lateral joint member is positioned between the lower end of the lateral wing of the ankle cuff and the upper end of the lateral wing of the foot bed member. The flexible lateral joint member includes a central base portion having radially spaced-apart first, second and third pin openings formed therein. The base portion of the flexible lateral joint member has a central opening formed therein. The flexible lateral joint member has first, second and third arms with inner and outer ends, extending outwardly from the base portion thereof. Fourth, fifth and sixth pin openings are formed in the outer ends of the first, second and third arms respectively.

As stated, the flexible lateral joint member is positioned at the inner side of the lower end of the lateral wing of the ankle cuff. When so positioned, the first, second and third pin members, which extend inwardly from the inner side of the lower end of the lateral wing of the ankle cuff, are received in the fourth, fifth and sixth pin openings in the flexible lateral joint member respectively. In that position, the first, second and third pin openings in the flexible lateral joint member register with the first, second and third slots formed in the lower end of the lateral wing of the ankle cuff and the central opening in the base portion of the flexible lateral joint member registers with the central opening formed in the central section of the lower end of the lateral wing of the ankle cuff. A connector element, such as a rivet or the like, extends through the central opening in the lower end of the lateral wing of the ankle cuff, through the central opening in the base position of the flexible lateral joint member and through the central opening in the central section of the upper end of the lateral wing of the foot bed member to hingedly connect the lateral wing of the foot bed member to the lateral wing of the ankle cuff.

The flexible joint members create greater resistance to hinged movement of the foot bed member and the ankle cuff thereof as the two members hingedly move to a greater degree with respect to one another in a plantarflexion and dorsiflexion direction. The outwardly curved inner sides of the lower ends of the medial and lateral wings of the ankle cuff and the outwardly curved outer sides of the upper ends of the medial and lateral wings of the foot bed member also permit a limited amount of inversion and eversion movement between the foot bed member and the ankle cuff. As seen in the drawings, the ankle brace of this invention is preloaded with some dorsiflexion. However, the ankle brace may be easily preloaded with plantarflexion.

A second embodiment of the hinged ankle brace of this invention is also illustrated and described. In the second embodiment, the outer sides of the upper ends of the medial and lateral wings of the foot bed member are outwardly curved. In the second embodiment, the outer sides of the lower ends of the medial and lateral wings of the ankle cuff are not outwardly curved or domed but are flat.

At least one strap is attached to the ankle cuff which is configured to secure a wearer's lower calf thereto.

It is therefore a principal object of the invention to provide an improved hinged ankle brace.

A further object of the invention is to provide a hinged ankle brace wherein the foot bed member of the ankle brace is hingedly connected to the ankle cuff of the ankle brace wherein the joint members between the foot bed members and the ankle cuff are comprised of a flexible material wherein the resistance to the hinged movement between the foot bed member and the ankle cuff increasingly resists the hinged movement of the two members as the hinged movement of the two members increases.

A further object of the invention is to provide a hinged ankle brace which not only permits a limited amount of plantarflexion and dorsiflexion movement between the ankle cuff and the foot bed member but also permits a limited amount of inversion and eversion movement therebetween.

These and other objects will be apparent to those skilled in the art.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DESCRIPTION OF THE PREFERRED EMBODIMENT

Figure 1:
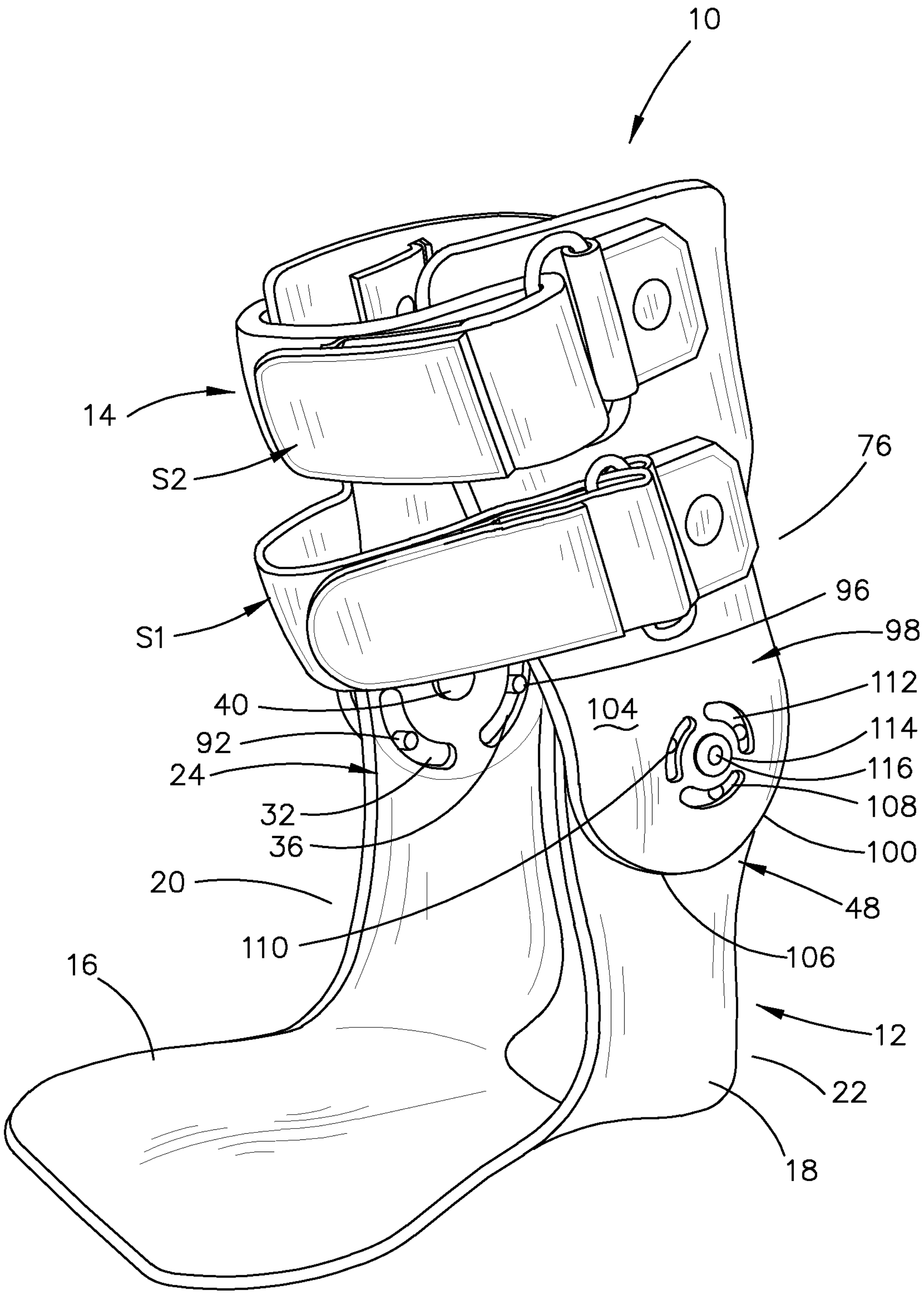
FIG. 1 is a perspective view of the ankle brace of this invention.
Figure 2:
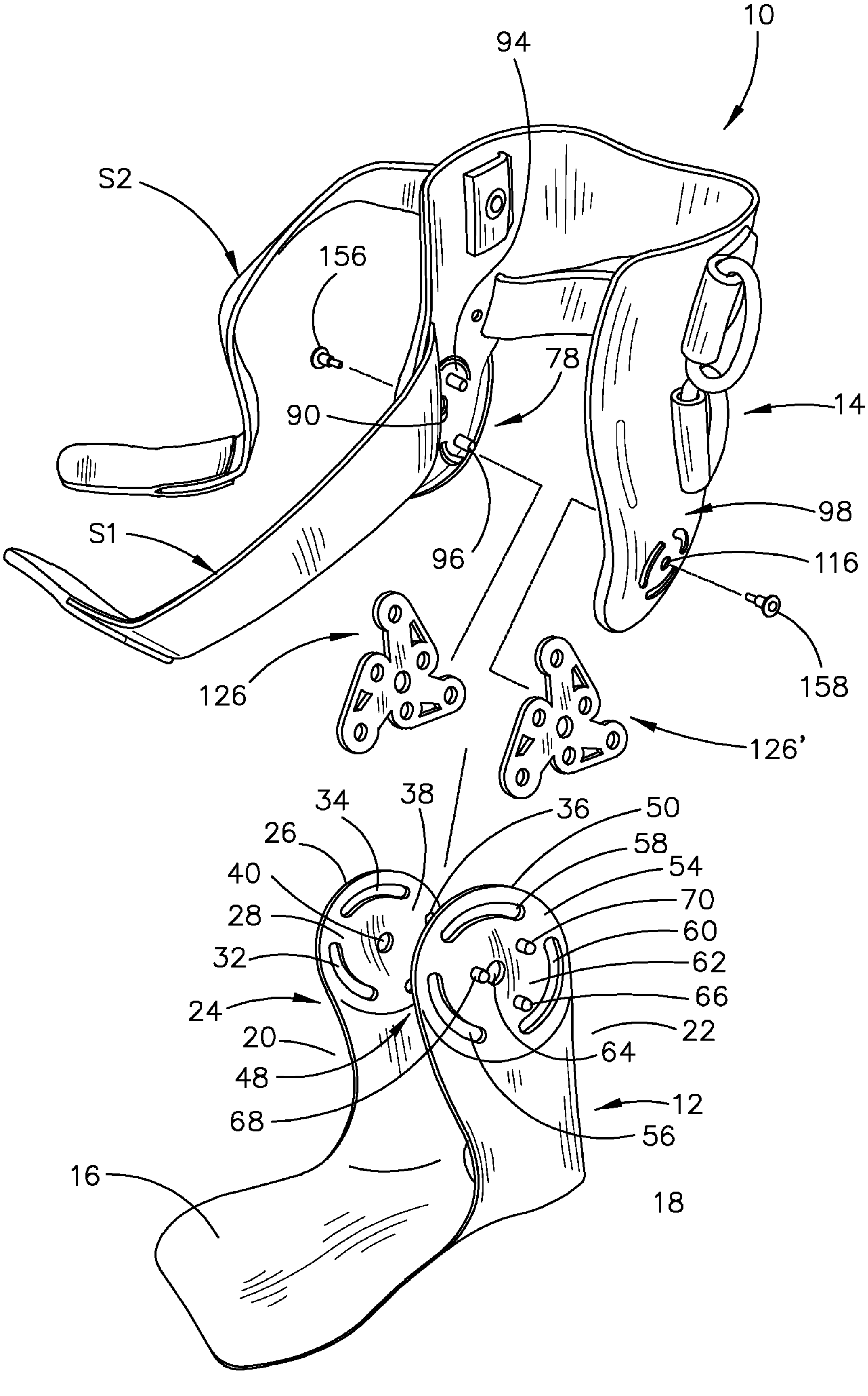
FIG. 2 is an exploded perspective view of the ankle brace of this invention.
Figure 3A:
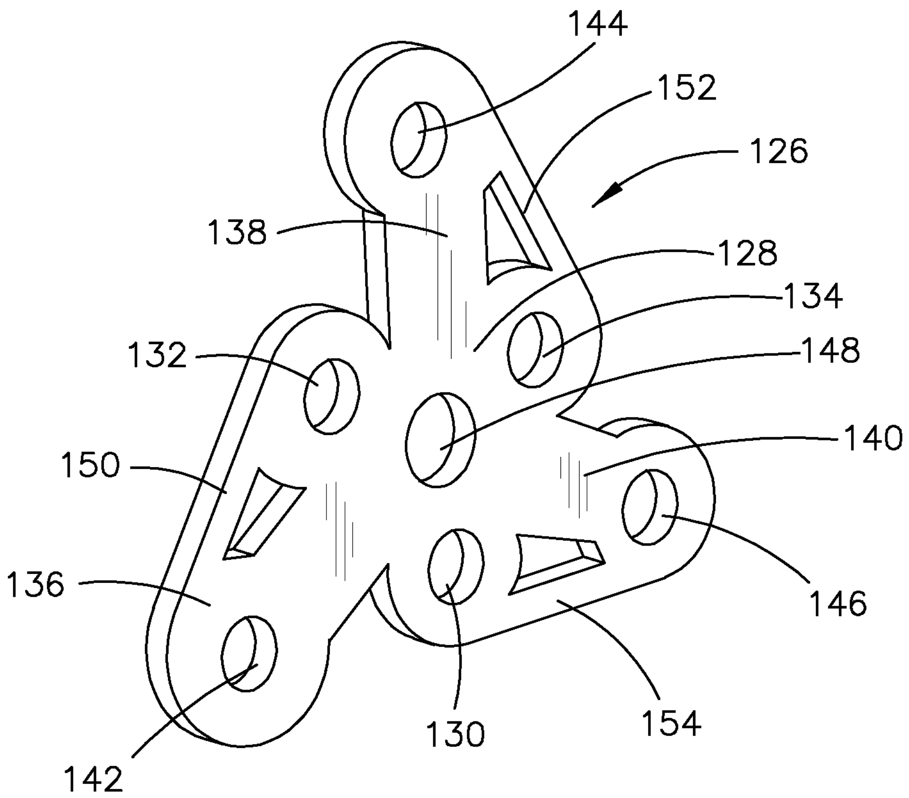
FIG. 3A is a perspective view of one of the flexible joint members of this invention.
Figure 3B:
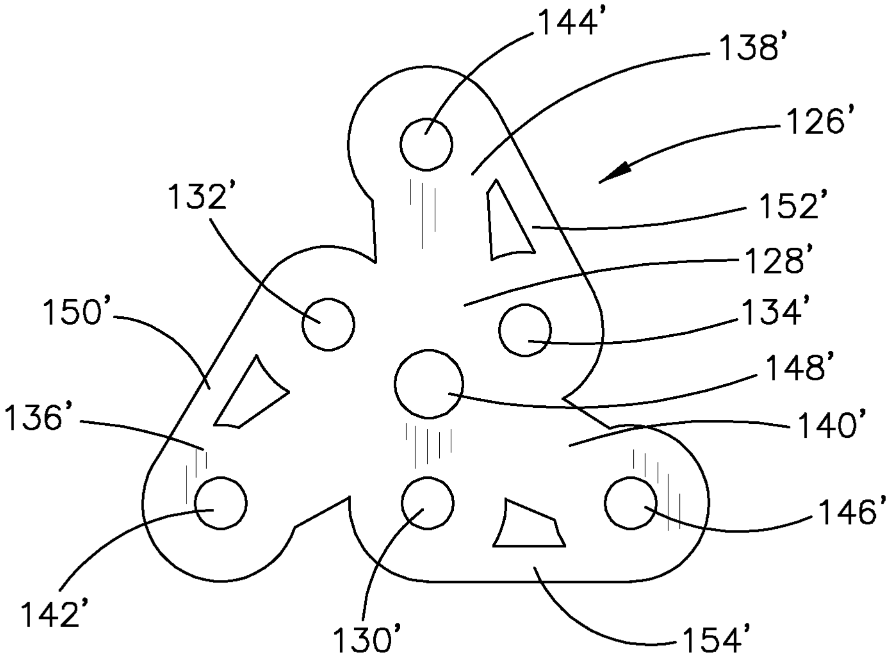
FIG. 3B is a plan view of the hinged joint member of FIG. 3A.
Figure 4:
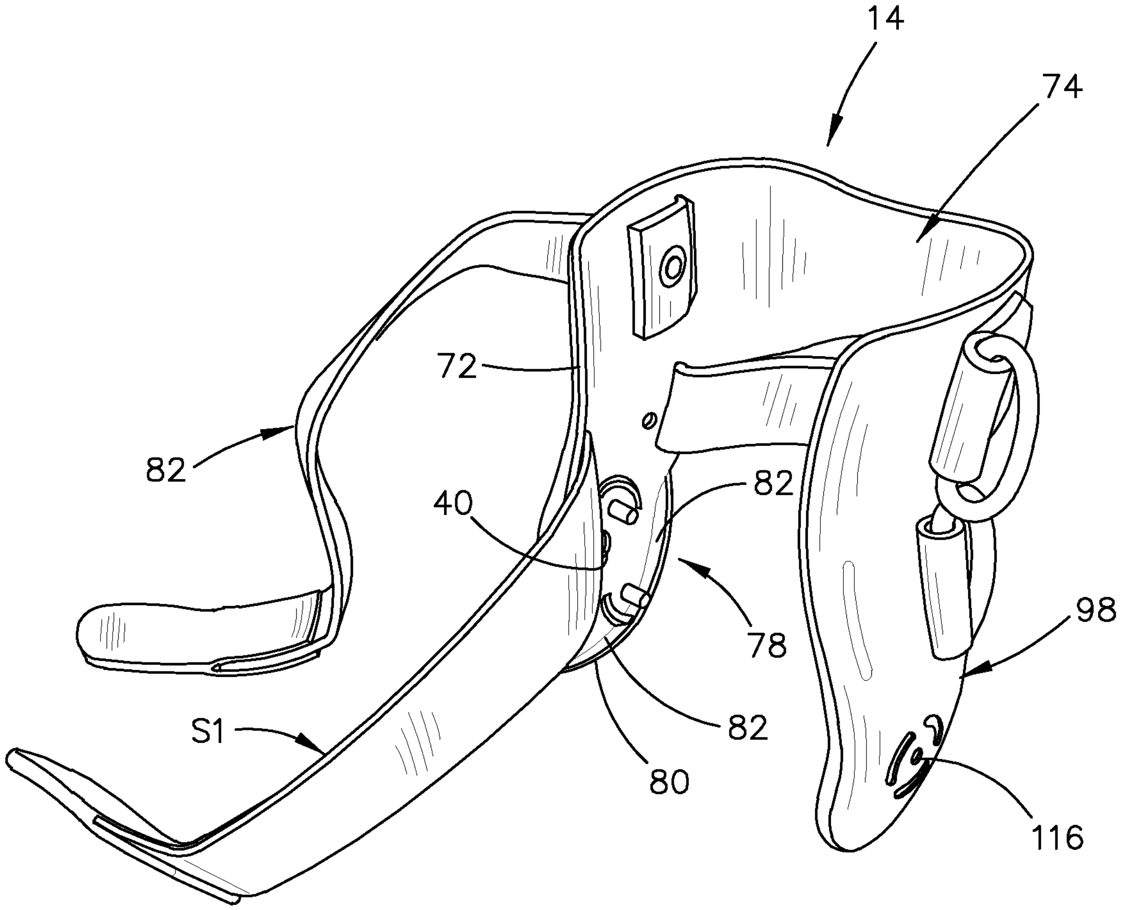
FIG. 4 is a front perspective view of the ankle cuff portion of this invention.
Figure 5:
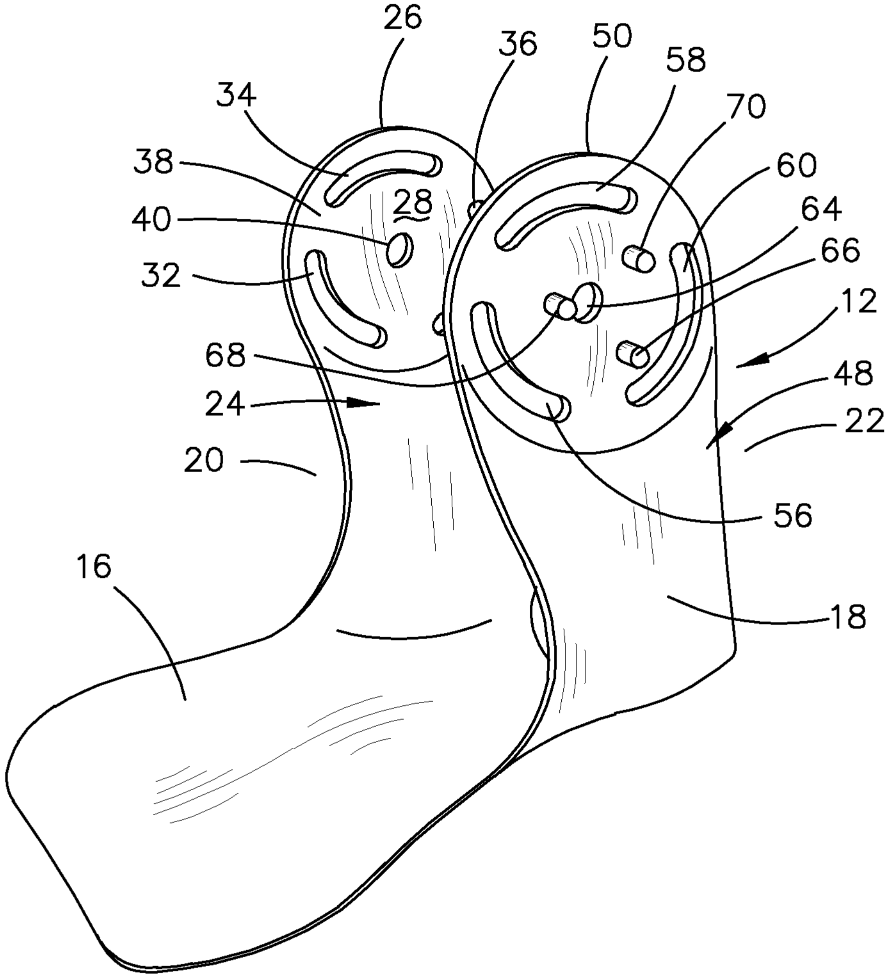
FIG. 5 is a perspective view of the foot bed member of this invention.
Figure 5A:
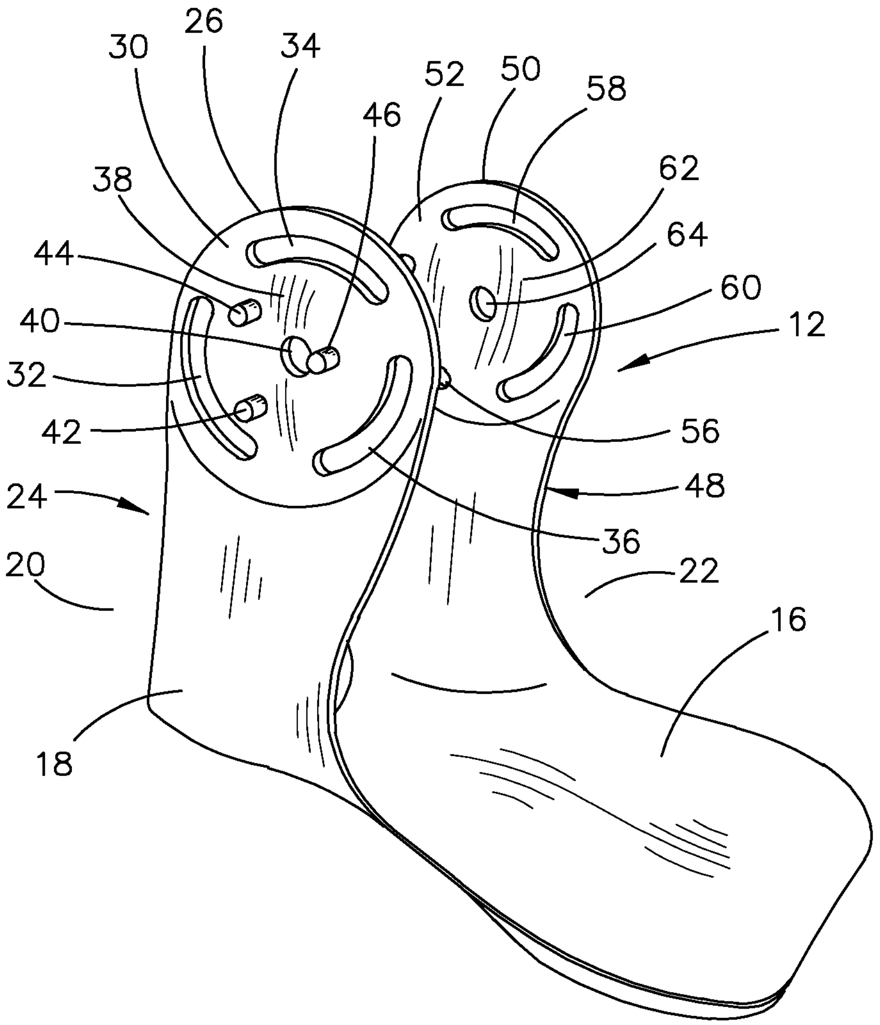
FIG. 5A is a perspective view which is a mirror image of FIG. 5.
Figure 6:
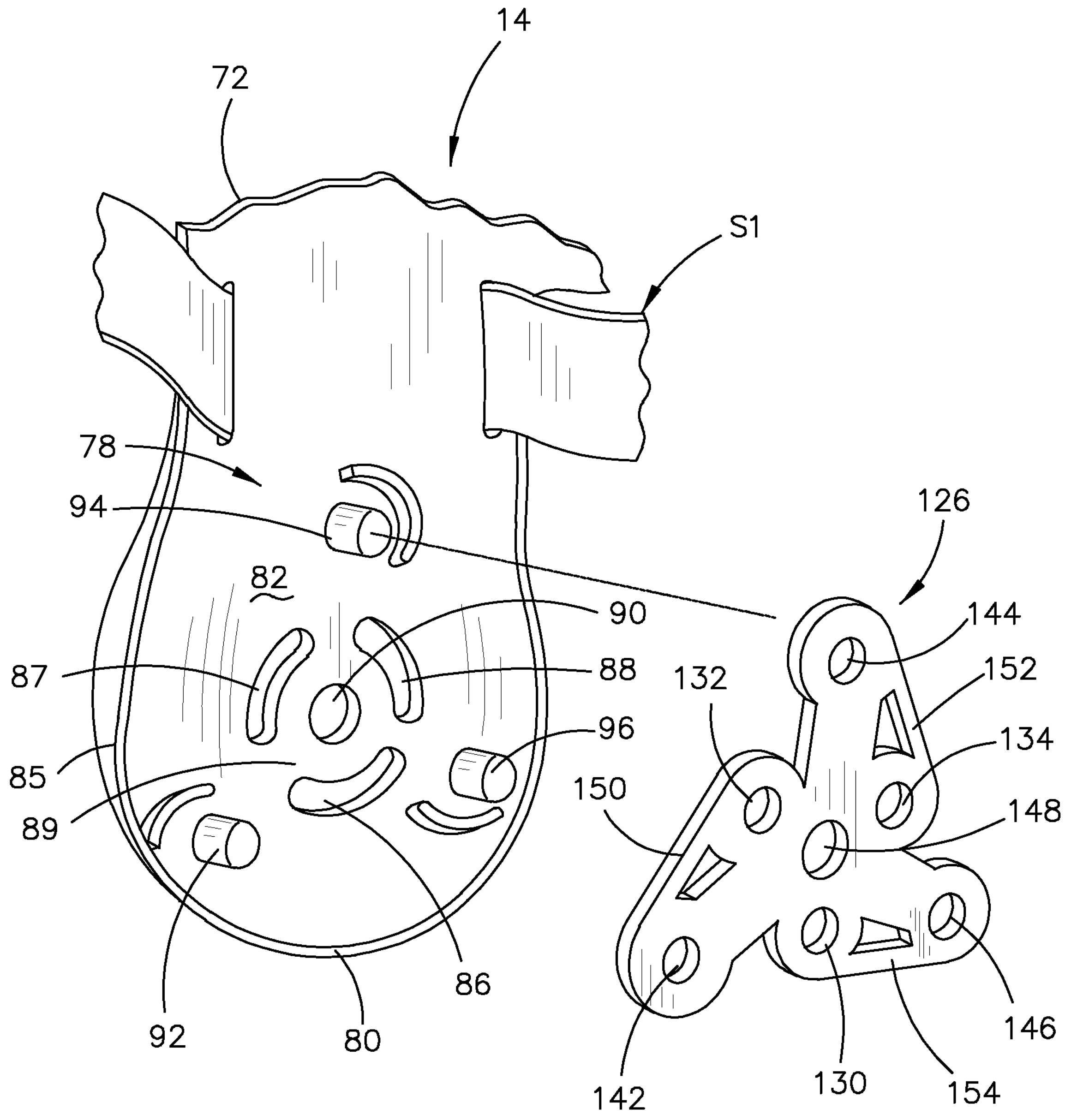
FIG. 6 is a partial exploded perspective view of the inner side of the medial wing of the ankle cuff of this invention and the medial joint member of this invention.
Figure 6A:
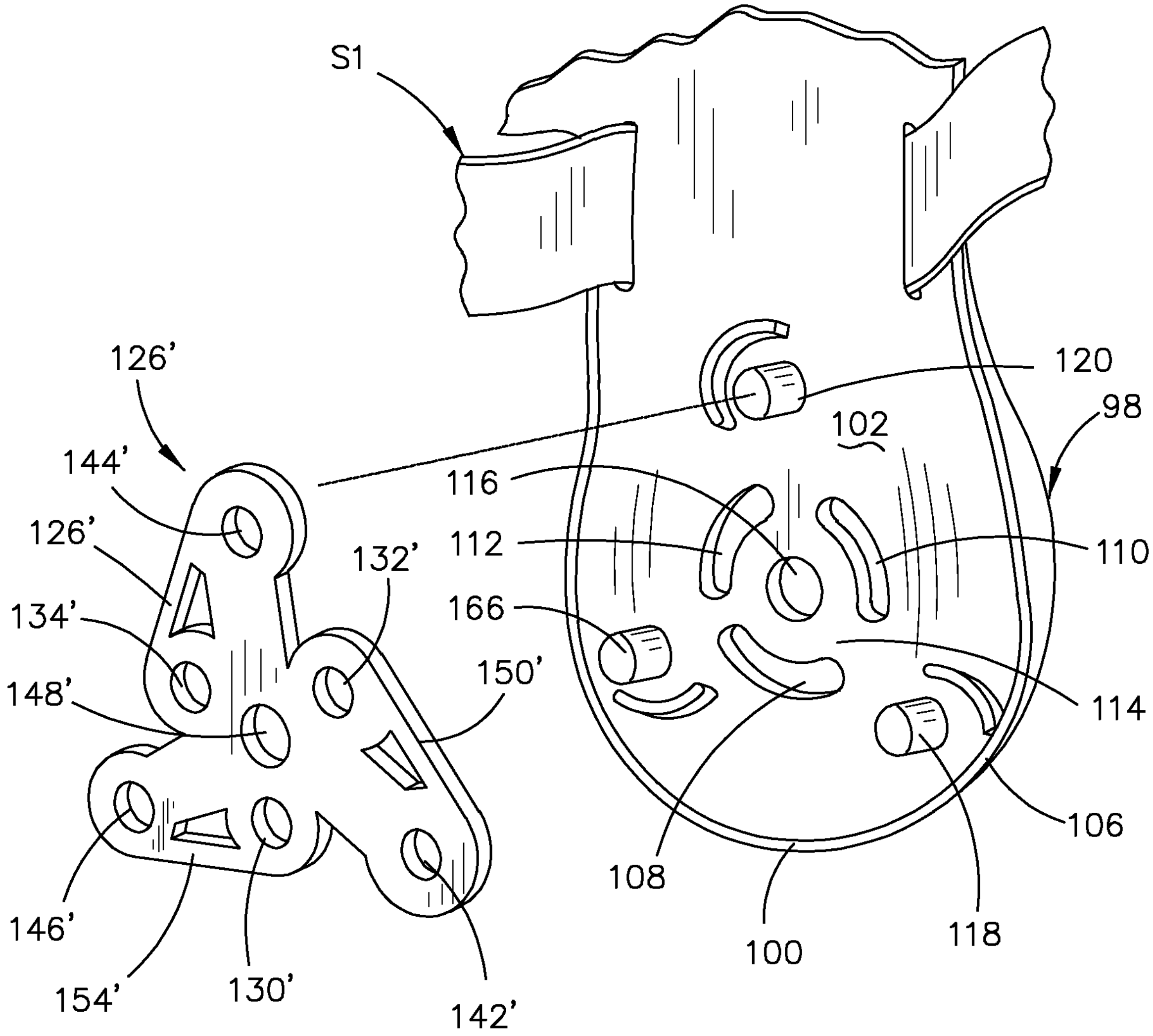
FIG. 6A is a partial exploded perspective view of the inner side of the lateral wing of the ankle cuff of this invention and the lateral joint member of this invention.
Figure 7:
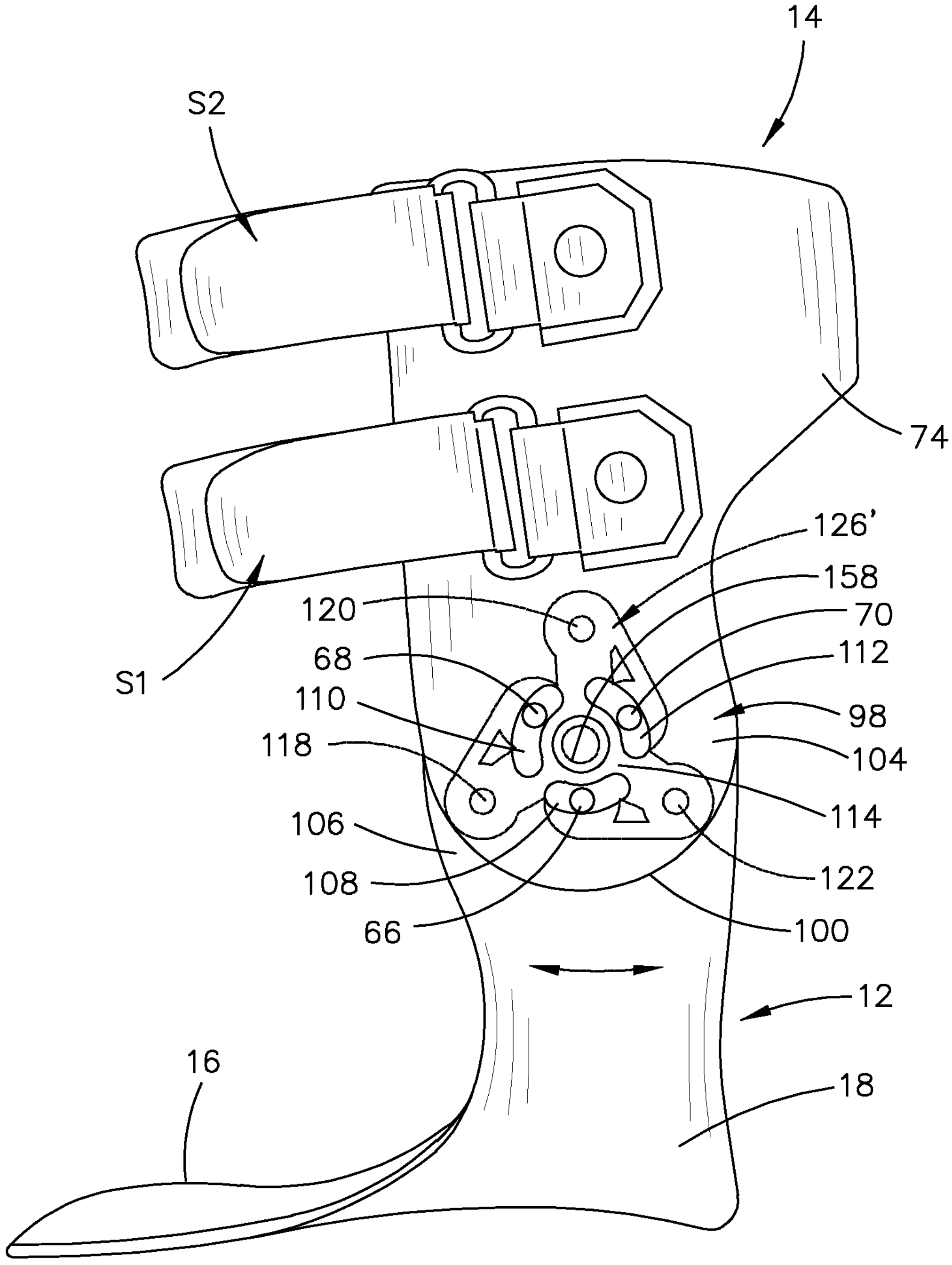
FIG. 7 is a side view of the lateral side of this invention with the lateral side of the joint member thereof being shown in broken lines.
Figure 8:
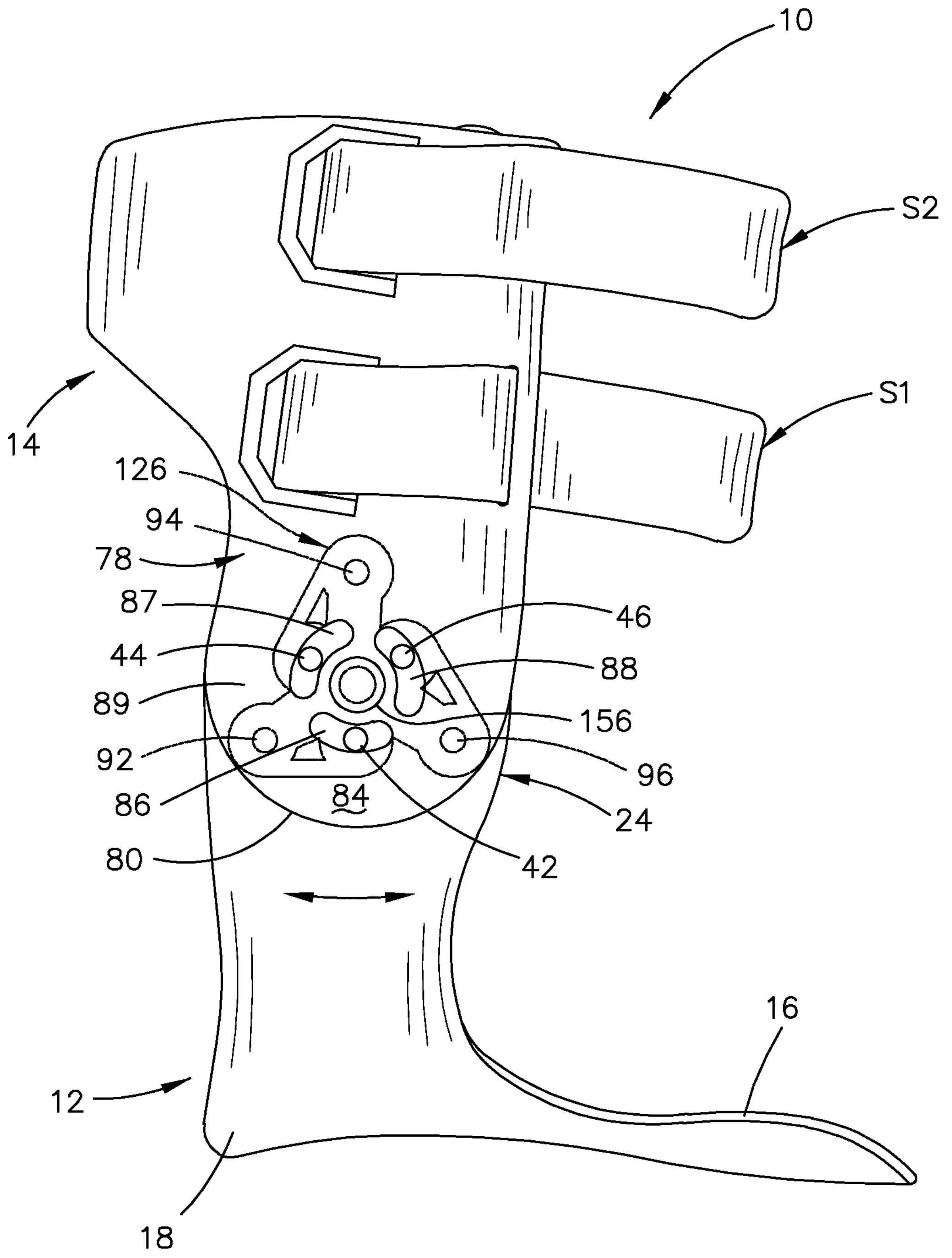
FIG. 8 is a side view of the medial side of the ankle brace of this invention with the medial joint member thereof being shown in broken lines.
Figure 9:
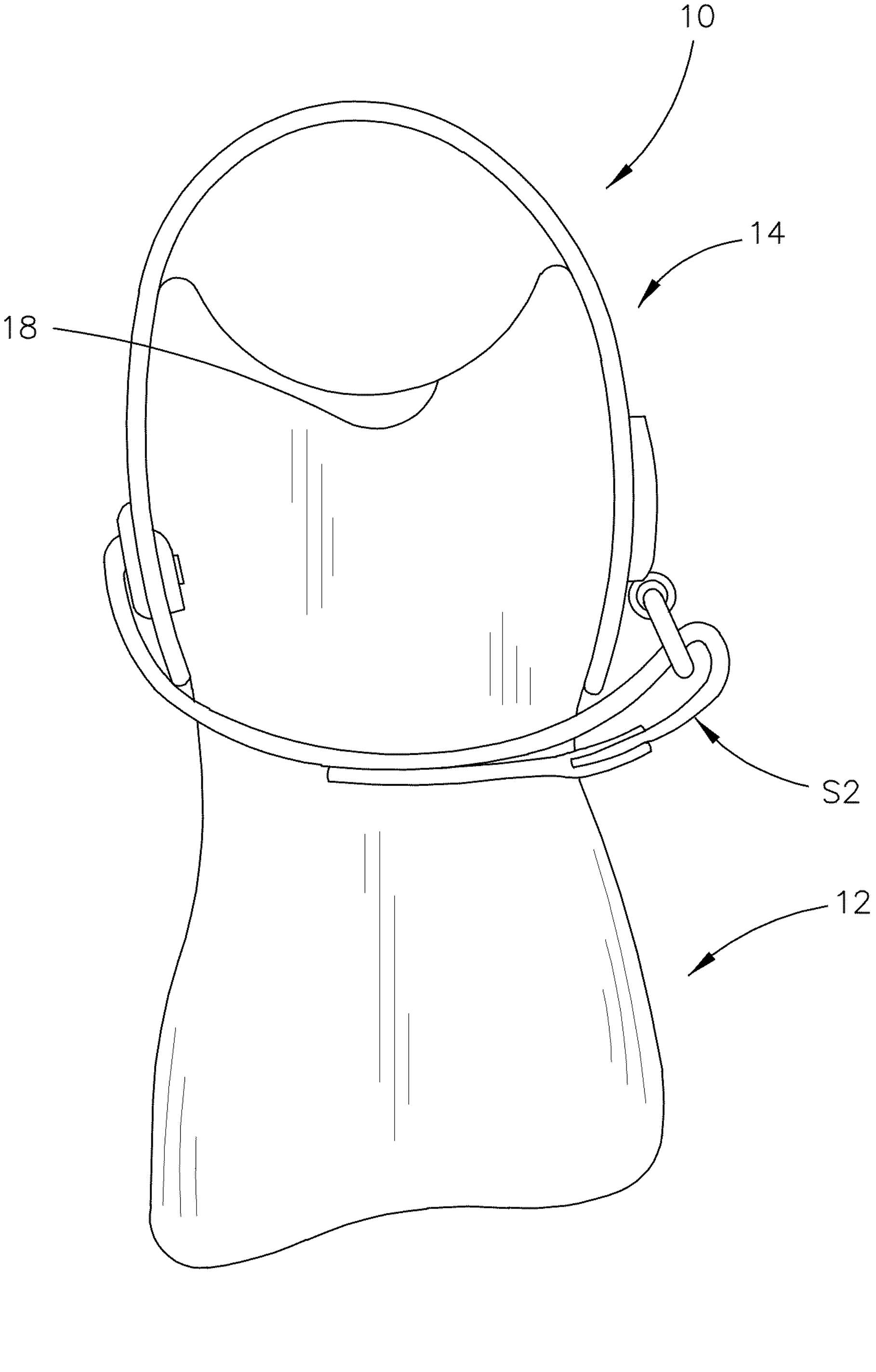
FIG. 9 is a top view of the ankle brace of this invention.
Figure 10:
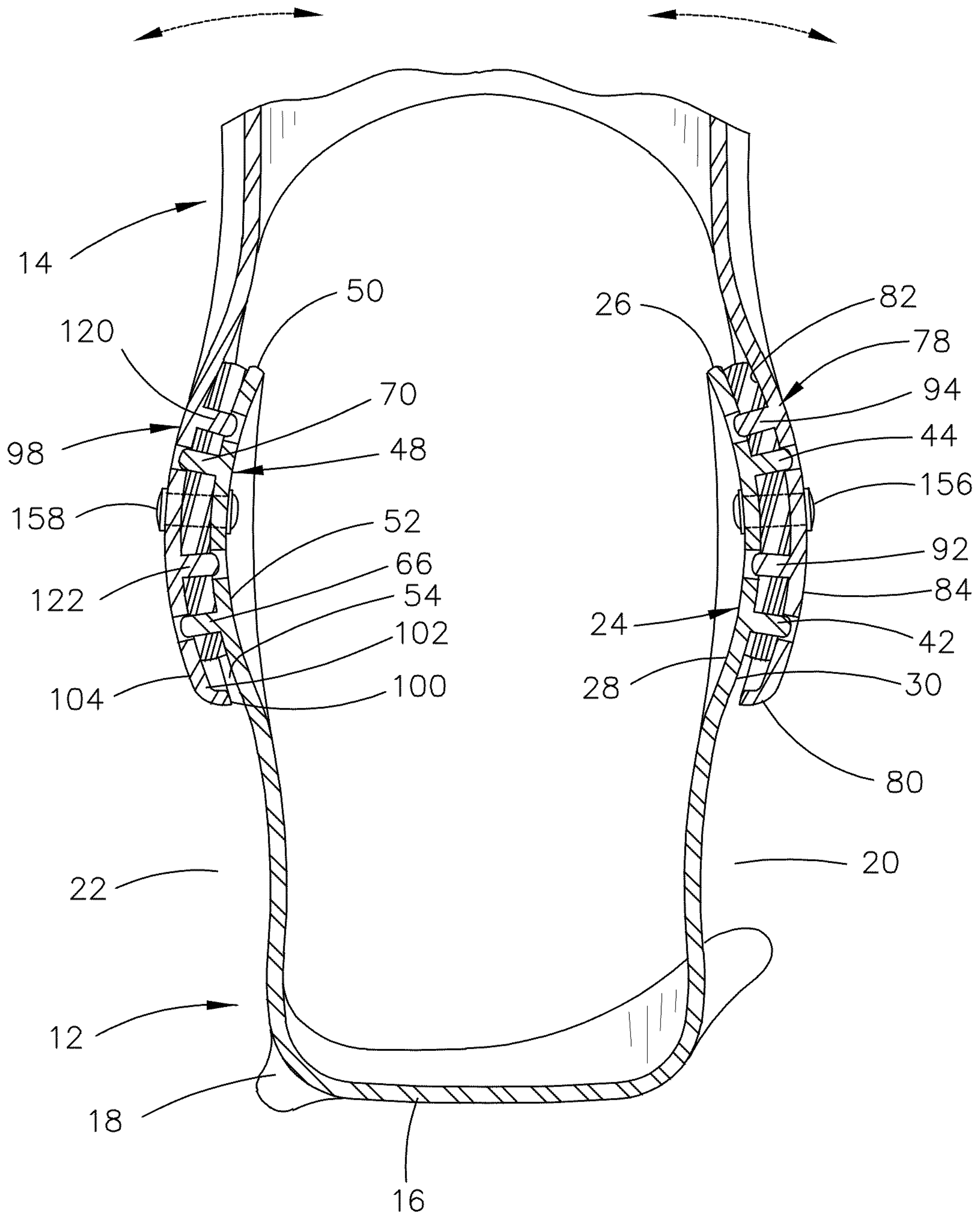
FIG. 10 is a partial sectional view of the ankle brace of this invention.

Embodiments are described more fully below with reference to the accompanying figures, which form a part hereof and show, by way of illustration, specific exemplary embodiments. These embodiments are disclosed in sufficient detail to enable those skilled in the art to practice the invention. However, embodiments may be implemented in many different forms and should not be construed as being limited to the embodiments set forth herein. The following detailed description is, therefore, not to be taken in a limiting sense in that the scope of the present invention is defined only by the appended claims.

The hinged ankle brace of this invention is designated by the reference numeral 10. Ankle brace 10 generally includes a foot bed member 12 and an ankle cuff 14 which are hingedly connected as will be described in detail hereinafter. The general shape of the foot bed member and the ankle cuff may vary. Ankle brace 10 will be described as being configured to be used with the left ankle and leg of a wearer. It should be understood that the ankle brace 10 could also be used to protect the right ankle of the wearer. The terms medial and lateral will apply to the left ankle brace with those terms being reversed for a right ankle brace. The brace 10 could also be easily designed to be a universal ankle brace suitable for use on either the right or left ankles.

Foot bed member 12 includes a foot plate 16 which is configured to underlie at least a portion of a foot of a wearer. Food pad member 12 also includes a heel portion 18 which is configured to receive a heel of the wearer. Foot bed member 12 will be described as having a medial side 20 and a lateral side 22. A medial wing 24 extends upwardly from the medial side 20 of the foot bed member 12. Medial wing 24 has a generally semi-circular upper end 26 with an inner side 28 and an outer side 30. The generally semi-circular upper end 26 of medial wing 24 has three radially spaced-apart and curved slots 32, 34 and 36 formed therein. The generally semi-circular upper end 26 of medial wing 24 has a central portion 38 which has a central opening 40 formed therein. Central portion 36 has three radially spaced-apart pin members 42, 44 and 46 extending outwardly therefrom. The pin members 42, 44 and 46 preferably have blunt outer ends.

The inner side 28 of the upper end 26 of medial wing 24 is outwardly curved as seen in the drawings. The outer side 30 of the upper end 26 of medial wing 24 is outwardly curved or domed as seen in the drawings.

A lateral wing 48 extends upwardly from the lateral side 22 of the foot bed member 12. Lateral wing 48 has a generally semi-circular upper end 50 with an inner side 52 and an outer side 54. The generally semi-circular upper end 50 of lateral wing 48 has three radially spaced-apart and curved slots 56, 58 and 60 formed therein. The general semi-circular upper end 50 of lateral wing 48 has a central portion 62 which has a central opening 64 formed therein. Central portion 62 has three radially spaced-apart pin members 66, 68 and 70 extending outwardly therefrom. The outer ends of pin members 66, 68 and 70 are preferably blunt. The inner side 52 of the upper end 50 of lateral wing 48 is outwardly curved as seen in the drawings. The outer side 54 of the upper end 50 of lateral wing 48 is outwardly curved or domed as seen in the drawings.

Ankle cuff 14 is designed to partially extend around the lower calf or leg of a person. Ankle cuff 14 includes a medial portion 72, a back portion 74 and a lateral portion 76. A medial wing 78 extends downwardly from the lower end of medial portion 72 and has a generally semi-circular lower end 80. Lower end 80 has an inner side 82 and an outer side 84. Preferably, medial wing 78 of ankle cuff 14 has an inwardly extending edge 85.

The lower end 80 of medial wing 78 of ankle cuff 14 has three radially spaced-apart and curved slots 86, 87 and 88 formed therein. The lower end 80 of medial wing 78 of ankle cuff 14 has a central portion 89 which has a central opening 90 formed therein. The inner side 82 of medial wing 78 has three radially spaced-apart pin members 92, 94 and 96 extending inwardly therefrom.

Preferably, the inner ends of the pin members 92, 94 and 96 are blunt. The inner side 82 of medial wing 78 is outwardly curved. The outer side 84 of medial wing 78 is outwardly curved or domed as seen in the drawings.

A lateral wing 98 extends downwardly from the lower end of lateral portion 76 of ankle cuff 14 and has a generally semi-circular lower end 100. Lower end 100 has an inner side 102 and an outer side 104. Preferably, the lower end 100 of lateral wing 98 has an inwardly extending edge 106. The lower end 100 of lateral wing 98 has three radially spaced-apart and curved slots 108, 110 and 112 formed therein. The lower end 100 of lateral wing 98 has a central portion 114 which has a central opening 116 formed therein. The inner side 102 of lateral wing 98 has three radially spaced-apart pin members 118, 120 and 122 which extend inwardly therefrom. Preferably, the inner ends of the pin members 118, 120 and 122 are blunt. The inner side 102 of lateral wing 98 is outwardly curved. The outer side 104 of lateral wing 98 is outwardly curved or domed.

The reference number 126 refers to a flat flexible medial joint member which hingedly connects medial wing 24 of foot bed member 12 to medial wing 78 of ankle cuff 14. Joint member 126 is comprised of a flexible polyurethane material or other similar material. Joint member 126 is flat and has an inner side and an outer side. Joint member 126 includes a central base portion 128 which had radially spaced-apart pin openings 130, 132 and 134 formed therein. Support arms 136, 138 and 140 extend outwardly from base portion 128 in a radially spaced-apart manner. Arms 136, 138 and 140 have pin openings 142, 144 and 146 formed in the outer ends thereof. Base portion 128 includes a central opening 148 formed therein. Joint member 126 includes a rib 150 which extends between base portion 128 and support arm 136, a rib 152 which extends between base portion 128 and support arm 138, and a rib 154 which extends between base portion 128 and support arm 140.

Joint member 126 is positioned at the inner side of lower end 80 of medial wing 78 of ankle cuff 14 as seen in the drawings. When so positioned, the pin members 92, 94 and 96, which extend inwardly from the inner side 82 of lower end 80 of medial wing 78, extend into the pin openings 130, 132 and 134 in the outer ends of the support arms 136, 138 and 140 respectively. When so positioned, the inner ends of the pin members 92, 94 and 96 protrude from joint member 126.

The reference numeral 126' refers to a flat flexible medial joint member which hingedly connects medial wing 24 of foot bed member 12 to lateral wing 76 of ankle cuff 14. Joint member 126' is comprised of a flexible polyurethane material or other similar material. Joint member 126' is flat and has an inner side and an outer side. Joint member 126' includes a central base portion 128' which has radially spaced-apart pin openings 130', 132' and 134' formed therein. Support arms 136', 138' and 140' extend outwardly from base portion 128' in a radially spaced-apart manner. Arms 136', 138' and 140' have pin openings 142', 144' and 146' formed in the outer ends thereof. Base portion 128' includes a central opening 148' formed therein. Joint member 126' includes a rib 150' which extends between base portion 128' and support arm 136', a rib 152' which extends between base portion 126' and support arm 138', and a rib 154' which extends between base portion 128' and support arm 140'.

Joint member 126' is positioned at the inner side 102 of lower end 100 of lateral wing 98 of ankle cuff 14 as seen in the drawings. When so positioned, the pin members 118, 120 and 122, which extend inwardly from the inner side 102 of lower end 104 of lateral wing 98, extend into the pin openings 130', 132', and 134' in the outer ends of the support arms 136', 138', and 140' respectively. When so positioned, the inner ends of the pin members 92', 94' and 96' protrude from joint member 126'. Rivet 156 extends through opening 90 in medial wing 78 of ankle cuff 14, through opening 148 in medial joint member 126 and through central opening 40 in medial wing 24 of foot bed member 12 to hingedly connect foot bed member 12 to ankle cuff 14 to rivet 158 extending through opening 116 in lateral wing 98, through opening 148 in lateral joint member 126' and through opening 64 in lateral wing 48 to hingedly connect foot bed member 12 to ankle cuff 14.

As seen, ankle cuff 14 includes a pair of adjustable straps S1 and S2 at the upper end thereof which may be wrapped around the wearer's leg.

Figure 11:
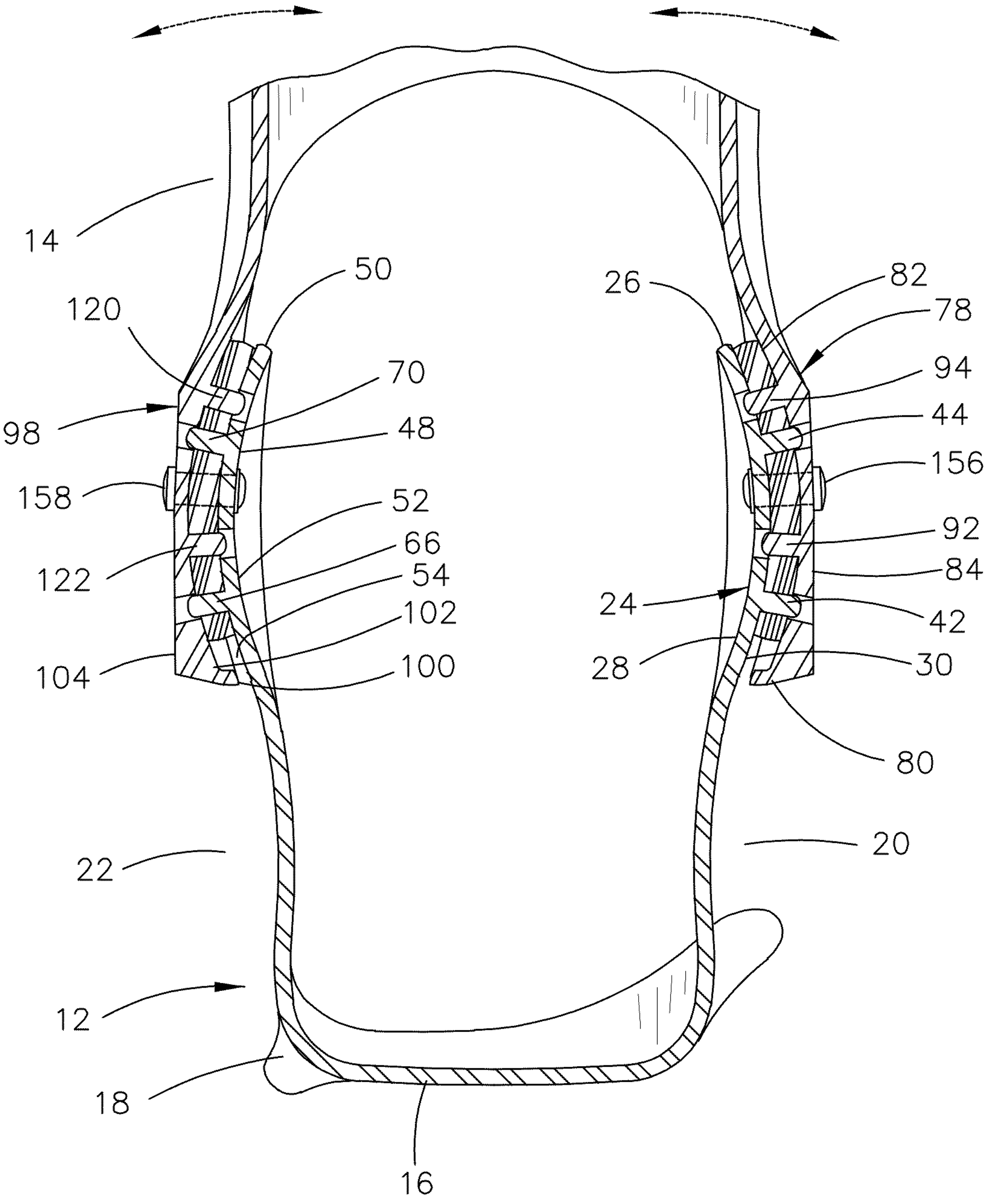
FIG. 11 is a partial sectional view of a second embodiment of the ankle brace of this invention.

In summary, the flexible joint members 126 and 126' and the related slots and pin member create greater resistance to hinged movement of the foot bed member 12 at the ankle cuff 14 as the two members hingedly move to a greater degree with respect to one another in a plantarflexion and dorsiflexion direction. The outwardly curved inner sides of the lower end of the medial and lateral wings of the ankle cuff 14 and the outwardly curved outer sides of the upper ends of the medial and lateral wings of the foot bed member 12 also permit a limited amount of inversion and eversion movement between the foot bed member 12 and the ankle cuff 14. The embodiment of FIG. 11 also permits a limited amount of inversion and eversion movement between the foot bed member and the ankle cuff 14.

Thus it can be seen that the invention accomplishes at least all of its stated objectives.

Although the invention has been described in language that is specific to certain structures and methodological steps, it is to be understood that the invention defined in the appended claims is not necessarily limited to the specific structures and/or steps described. Rather, the specific aspects and steps are described as forms of implementing the claimed invention. Since many embodiments of the invention can be practiced without departing from the spirit and scope of the invention, the invention resides in the claims hereinafter appended.

I claim:

1. An ankle brace comprising:

a foot bed member configured to engage a foot of a wearer;

a lower leg cuff configured to engage a lower leg of the wearer, the lower leg cuff being hingedly connected to the foot bed member such that the lower leg cuff is pivotable with respect to the foot bed member about an axis in a limited range of motion that includes a neutral position; and a flexible medial joint member configured to progressively increase resistance to pivotal movement as the lower leg cuff pivots with respect to the foot bed member about the axis away from the neutral position; a first set of pins securing one of the foot bed member and the lower leg cuff to the flexible medial joint member at first pin locations radially spaced apart from the axis by a first radial spacing distance and a second set of pins securing the other of the foot bed member and the lower leg cuff to the flexible medial joint member at second pin locations radially spaced apart from the axis by a second radial spacing distance greater than the first radial spacing distance.

2. The ankle brace as set forth in claim 1, wherein the flexible medial joint member comprises resiliently flexible material.

3. The ankle brace as set forth in claim 2, wherein the flexible medial joint member is configured to yieldably bias the lower leg cuff toward the neutral position.

4. The ankle brace as set forth in claim 1, wherein the flexible medial joint member comprises a central portion, the axis intersecting the central portion.

5. The ankle brace as set forth in claim 1, wherein the flexible medial joint member further comprises a plurality of lobes circumferentially spaced apart about the axis, each first pin location being located on a respective one of the plurality of lobes.

6. The ankle brace as set forth in claim 5, wherein the flexible medial joint member further comprises a plurality of arms circumferentially space apart about the axis such that each arm is interleaved between an adjacent pair of the lobes, each second pin location being located on a respective one of the plurality of arms.

7. The ankle brace as set forth in claim 6, wherein as the lower leg cuff pivots with respect to the foot bed member about the axis, the first pins rotate with respect to the second pins about the axis causing the arms to resiliently bend, whereby the flexible medial joint member progressively increases resistance to pivotal movement.

8. The ankle brace as set forth in claim 7, wherein each arm has opposing circumferential edges and wherein each lobe has opposing circumferential edges spaced apart from adjacent circumferential edges of adjacent arms.

9. The ankle brace as set forth in claim 8, wherein a limit of the limited range of motion is defined by a rotational position at which at least one arm bends so that one of the circumferential edges thereof stops against the circumferential edge of one of the adjacent lobes.

10. An ankle brace comprising:

a foot bed member configured to engage a foot of a wearer;

a lower leg cuff configured to engage a lower leg of the wearer, the lower leg cuff being hingedly connected to the foot bed member such that the lower leg cuff is pivotable with respect to the foot bed member about an axis for plantarflexion and dorsiflexion and the lower leg cuff is further movable in relation to the foot bed to permit a more limited amount of inversion and eversion; a first set of pins connecting the first flexible medial joint member to the first foot bed wing and the first cuff wing and a second set of pins connecting the second flexible medial joint member to the second foot bed wing and the second cuff wing such that the first and second flexible medial joint members are configured to progressively increase resistance to pivotal movement as the lower leg cuff pivots with respect to the foot bed member about the axis.

11. The ankle brace of claim 10, wherein the foot bed member comprises first and second foot bed wings and wherein the lower leg cuff comprises first and second cuff wings.

12. The ankle brace of claim 11, wherein each foot bed wing comprises a dome-shaped bearing surface and wherein each cuff wing comprises a dome-shaped bearing surface.

13. The ankle brace of claim 12, wherein the first foot bed wing and the first cuff wing overlap one another such that an inner one of the respective dome-shaped bearing surfaces nests within the other respective dome-shaped surface to form a first spherical bearing;

wherein the second foot bed wing and the second cuff wing overlap one another such that an inner one of respective dome-shaped bearing surfaces nests within the other respective dome-shaped surface to define a second spherical bearing; and wherein the first and second spherical bearings permit the more limited amount of inversion and eversion.

14. The ankle brace of claim 13, further comprising a first flexible medial joint member between the dome-shaped surfaces of the first foot bed wing and the first cuff wing and a second flexible medial joint member between the dome-shaped surfaces of the second foot bed wing and the second cuff wing.

* * * * *